United States Patent
Perlman

[11] Patent Number: 6,156,711
[45] Date of Patent: Dec. 5, 2000

[54] THICKENED BUTYROLACTONE-BASED NAIL POLISH REMOVER WITH APPLICATOR

[75] Inventor: Daniel Perlman, Arlington, Mass.

[73] Assignee: Brandeis University, Waltham, Mass.

[21] Appl. No.: 09/260,752

[22] Filed: Mar. 1, 1999

Related U.S. Application Data

[63] Continuation-in-part of application No. 09/144,189, Aug. 31, 1998, abandoned.

[51] Int. Cl.$^7$ .................................................. C11D 3/20
[52] U.S. Cl. ............................................ 510/118; 510/505
[58] Field of Search .................................... 510/138, 201, 510/505, 118

[56] References Cited

U.S. PATENT DOCUMENTS

| | | | |
|---|---|---|---|
| 4,804,486 | 2/1989 | Day | 252/153 |
| 5,024,779 | 6/1991 | Helioff et al. | 252/162 |
| 5,641,890 | 6/1997 | Wesley et al. | 44/266 |

FOREIGN PATENT DOCUMENTS

| | | |
|---|---|---|
| 270050 | 2/1991 | Czech Rep. . |
| 54-46846 | 4/1979 | Japan . |

*Primary Examiner*—John R. Hardee

[57] ABSTRACT

A thickened nail polish-lacquer removing composition having a smooth, substantially non-granular consistency. The composition is substantially non-irritating and non-sensitizing to the skin surrounding the fingernails and toenails. Upon drying, the residue of the lacquer-removing composition is water-soluble. The composition includes from 51% to 99.9% by weight of butyrolactone organic solvent and/or a propylene glycol derivative solvent and from 0.1% to 5% by weight of at least one water-soluble thickening agent capable of functioning in the absence of a neutralizing agent, and which is present in an amount effective to produce an absolute kinematic viscosity at 20° C. of from 250–10,000 cp.

31 Claims, No Drawings

6,156,711

THICKENED BUTYROLACTONE-BASED NAIL POLISH REMOVER WITH APPLICATOR

RELATED APPLICATION

This application is a continuation-in-part of Perlman, U.S. patent application Ser. No. 09/144,189, filed Aug. 31, 1998, now abandoned, entitled THICKENED PROPYLENE GLYCOL ETHER NAIL POLISH REMOVER, which is hereby incorporated by reference in its entirety.

BACKGROUND OF THE INVENTION

1. Field of the Invention

This invention relates to the field of cosmetics products, specifically to the field of liquid nail polish removers.

2. Background

The following description is provided solely to assist the understanding of the reader. None of the references cited are admitted to be prior art to the present invention.

Organic solvent-based products have been marketed for many years for removing nail polishes from fingernails and toenails. In recent years, water-based nail polishes have also emerged, and are removed using similar solvent-containing products. For reasons of economy and efficacy, the most common solvent systems used to remove such nail polishes (also known as lacquers) have been acetone and ethyl acetate. However, many problems including skin irritation, and skin and cuticle desiccation are associated with the use of these solvents, and many patents have been issued to remediate these problems.

For example, Curtis (U.S. Pat. No. 4,485,037) describes an aqueous acetone-based nail polish remover whose tendency to remove water from the fingernail and skin is reduced by incorporating an amine salt of a fatty acid amide of a hydrolyzed collagen, and a fatty acid-substituted tri-alkylamine cationic surfactant. Hofmann (U.S. Pat. No. 4,824,662) describes an acetone or ethyl acetate solvent-based nail polish remover containing a surfactant and an amidoamine salt of hydrolyzed soy protein to reduce the skin and nail water removal properties of the solvent. Hofmann (U.S. Pat. No. 5,077,038) also describes an acetone and/or ethyl acetate-based nail polish remover in which the solvent concentration is limited to approximately 60–80% by weight, and water is added (approximately 20–40% by weight). The salt of a hydrolyzed soy protein and cocamidopropyl dimethylamine propionate are added to prevent drying of the nail and surrounding skin.

Helioff et al. (U.S. Pat. No. 5,024,779) describe a creamy viscous nail polish remover based upon acetone, methyl ethyl ketone, ethyl acetate, and/or butyrolactone, and containing up to about 3% by weight of neutralized crosslinked maleic anhydride-alkyl vinyl ether copolymer gel, and a humectant. Day (U.S. Pat. No. 4,804,486) describes a cream-like nail polish remover utilizing gamma-butyrolactone solvent, and a neutralized acrylic acid-type gelling agent. Remz et al. (U.S. Pat. No. 5,294,435) describe an acetone-based nail polish remover containing a conditioning agent, e.g., stearic acid and triethanolamine, and a suspending agent, e.g., styrene methacrylic polymer, to avoid precipitation of the conditioner. Miner et al. (U.S. Pat. No. 5,342,536) describe an acetone-based nail polish remover that includes gelatin and also glycerin to hold the gelatin in suspension. Faryniarz et al. (U.S. Pat. No. 5,486,305) describe an acetone and/or ethyl acetate-based nail polish remover which contains a diester compound, and a humectant and emollient for conditioning the cuticle and nails. Appell (U.S. Pat. No. 5,027,839) describes a device to protect the skin from irritation caused by these nail polish remover solvents.

Solvent systems other than acetone and ethyl acetate have been described in the patent literature for nail polish lacquer removers, but have met with limited commercial success. These alternative systems have distinct drawbacks including health risks and environmental toxicity problems. For example, Adams (U.S. Pat. No. 4,543,206) describes a non-flammable methylene chloride-based liquid solvent system. There is a health risk associated with inhalation of methylene chloride, and environmental disposal of chlorinated hydrocarbons poses a problem. Dotolo et al. (U.S. Pat. No. 5,346,652) describe a non-aqueous fingernail polish remover based upon a d-limonene, N-methyl pyrrolidone (abbreviated NMP), and cetyl acetate solvent system. However, d-limonene is harmful if swallowed, can be irritating, causes drying, reddening, and sensitization of the skin, and is moderately to highly irritating to the eyes (MSDS, d-limonene, Florida Chemical Co., Inc., Winter Haven, Fla.). Moreover, NMP is now listed an environmentally contaminating toxic solvent under the U.S. Environmental Protection Agency (abbreviated EPA) regulations, and is so-listed (SARA Title III, sec. 313). Similarly, Bayless (U.S. Pat. No. 5,372,742) describes a non-aqueous liquid cleaner suited for removing nail polish, based upon d-limonene, ethyl lactate, and cetyl acetate.

Several patents have focussed on thickener or gelling systems for nail polish lacquer removers. For example, Minton et al. (U.S. Pat. No. 4,197,212) describe an acetone or ethyl acetate-based nail polish remover which contains a hydroxypropyl cellulose acetate gelling agent which provides a Brookfield viscosity of 1,000 to 10,000 cp, and which leaves a beneficial residual film on the nail. Miner (U.S. Pat. No. 5,543,085) describes a thickened laquer-remover such as acetone-ethyl acetate thickened with an acrylate/vinyl acetate polymer, in which an electrolyte is added to the formulation to avoid a slimy or tacky residue on the nail and finger upon solvent evaporation.

As discussed above, several non-acetone/ethyl acetate organic solvents, including chlorinated hydrocarbons, N-methylpyrrolidone (NMP), and d-limonene, have been previously suggested for use in nail polish removers. However, these solvents have been either listed as pollutants on the HAP and/or SARA lists of the EPA, or have been implicated as toxic substances, respiratory irritants, skin irritants, or skin sensitizers, and consequently are relatively undesirable for use in consumer products. While the common EPA-unlisted solvents including acetone and ethyl acetate are currently used in most nail polish remover products, they are undesirable for several reasons including their unpleasant smell, their vapors being irritating to the eyes, their excessive volatility, and their being desiccating and irritating to the cuticle and skin around the nail. Acetone is also known to cause bronchial irritation, and skin erythema via topical exposure.

Among recent patents for nail polish removing compositions, the following are typical of compositions which utilize acetone or ethyl acetate as the primary active solvent: U.S. Pat. No. 5,543,085 by Miner, U.S. Pat. No. 5,486,305 by Faryniarz et al., U.S. Pat. No. 5,342,536 by Miner et al., U.S. Pat. No. 5,294,435 by Remz et al., U.S. Pat. No. 5,024,779 by Helioff et al., U.S. Pat. No. 5,077,038 by Hofmann, U.S. Pat. No. 4,824,662 by Hofmann, U.S. Pat. No. 4,485,037 by Curtis, and U.S. Pat. No. 4,197,212 by Minton et al.

SUMMARY OF THE INVENTION

This invention concerns a substantially non-volatile Liquid Nail Polish Remover (abbreviated LNPR) based upon the organic solvent, gamma butyrolactone (abbreviated GBL) and/or propylene glycol ether solvents, and to devices, compositions and methods for utilizing the solvent safely, practically and cost-effectively. Compared to conventional solvents, acetone and ethyl acetate, GBL is very costly. However, its low volatility allows very small (and thus cost-effective) quantities of the solvent to be applied, and to persist and dissolve nail lacquer on the surface of a fingernail or toenail. A reusable dip-applicator device, such as a small brush located in the lid of the LNPR container, is used for withdrawing and applying microliter quantities of the LNPR to nails. This highly efficient method of applying GBL does not work with highly volatile solvents, such as acetone and ethyl acetate, which evaporate before they can dissolve a lacquer coating. With acetone and ethyl acetate, generally a saturating volume of the solvent must be instilled into an absorbent pad or cotton ball which is then rubbed back and forth over a nail until a lacquer dissolves. Such a volume is commonly 0.2–0.5 ml or even more.

The present invention also concerns the coordinate use of solvent thickener with GBL. By placing the GBL solvent (preferably thickened) in a narrow-necked bottle, the GBL is accessible by dip-applicator, but is rendered more resistant to misuse, e.g., ingestion by children. The thickener is preferably pH-stable (i.e., chemically stable and functionally tolerant to changes in pH) so that the LNPR will remain thickened, even as its pH of the solution changes over its lifetime.

A method has also been found for treating and improving a cellulosic thickener (hydroxypropylcellulose) which has been dispersed in GBL. The normally granular-textured cellulosic dispersion is sheared to produce a smooth-textured thickened GBL solution. The resulting solution can then be treated, e.g., filtered and/or centrifuged, to remove residual large clumps. Alternatively, the clumps can be removed by centrifugation or filtering alone.

In preferred embodiments, the LNPR and its dried residue are water-soluble, biodegradable, and its vapors are not irritating to the eyes. As stated above, in contrast to acetone and ethyl acetate-based removers, the GBL-based LNPR is substantially non-volatile (unless volatile liquids, e.g., co-solvents, are added), causes little drying of the skin around the nail, and causes no skin irritation or sensitization upon repeated application, even in the absence of any humectant or emollient. Moreover, in the absence of an electrolyte, the remover composition leaves no gummy or sticky residue after solvent evaporation, or after wiping the nail polish/solvent residue from the nail. Furthermore, the remover composition is especially useful for loosening and removing hard-to-remove so-called "glitter" nail lacquers which contain suspended flecks of solvent-inert material such as polyester film.

Thus, in a first aspect, the invention provides a safety-enhanced packaged liquid nail polish-lacquer removing composition. The composition includes a nail polish-lacquer removing solution which is non-irritating and non-sensitizing to the skin surrounding nails. The remover includes between 51% and 100% by weight of thickened butyrolactone solvent, preferably from 70% to 99.9%, more preferably from 80% to 99.9%, packaged in a narrow-necked container, with the narrow neck of the container serving to retard or block the flow of solution out of the container when the container is tipped on its side or inverted. There is a maximum of 100 ml (or 3 fluid ounces) of the solution in the container. The composition also includes a reusable applicator device for applying microliter quantities of the solution to each nail.

As small volumes enhance the safety by reducing the overall toxicity hazard of ingestion, preferably there is a maximum of 30 ml (or 1 fluid ounce) of the solution in the container.

In preferred embodiments, the applicator device is an applicator brush, porous foam swab or pad, a hollow tube, an eye dropper, a dip stick or a combination of those devices. In preferred embodiments, the reusable applicator device is attached to a lid which covers the container.

In preferred embodiments, the solution contains at least one thickening agent present in an amount effective to produce an absolute kinematic viscosity at 20° C. of from 250–10,000 cp, preferably from 1000–10,000 cp, more preferably from 2000–8000 cp. Preferably the thickening agent functions in the absence of a neutralizing agent, preferably providing thickening over a pH range of at least pH 5–9, more preferably 4–9, or 5–10, or 4–10.

To further enhance safety by reducing the danger of ingestion, in preferred embodiments the solution also contains a bittering agent.

In addition, as the composition is adapted for repetitive use, such that an applicator will be contacted to a fingernail or toenail many times during use of a container of remover, it is preferable that the remover resists growth of microbes (e.g., bacteria and/or fungi) and still more preferably kills any microbes carried into the container. Thus, preferably the solution in this and the following aspects does not contain a substantial concentration of water, preferably the water content is less than 5% by weight, more preferably less than 2%, and most preferably less than 1%. Advantageously the remover solution is formulated without water (though there may still be a small amount of water absorbed from the atmosphere).

Also in view of the repetitive use, which can carry microbes into a container of the remover, one or more antimicrobial agents, e.g., antibacterial agents, can advantageously be included in the remover solution or composition of this and/or following aspects. For example, methylparaben and propylparaben (e.g., as specified in Day, supra) can be used. Preferred concentrations so of these agents are from 0.15 to 0.3% by weight total, with the methylparaben at approximately twice the concentration of the propylparaben (e.g., 0.2% and 0.1% by weight respectively). Other antibacterial and/or antifungal agents can also be used as recognized by those skilled in the art.

Additional embodiments are as described for the aspect below. The solution may contain additional components as described for nail polish-lacquer removing compositions below.

In related aspects, the solution and its components, especially the solvent and thickening components of the solution, are as described for other aspects herein.

The term "nail polish-lacquer" refers to materials commonly used for providing a protective and/or visual coating on fingernails and/or toenails, including materials referred to as nail polish, nail polish-lacquer, nail enamel, and similar names.

The term "butyrolactone" refers to a four carbon lactone, which is thus a four carbon cyclic ester. Highly preferred is gamma butyrolactone, which is also known by the names dihydro-2(3H)-furanone, and 4-butyrolactone. Indication that a nail polish-lacquer remover or a thickener in the polish remover is "tolerant to pH changes" or "pH stable" means that the thickening persists over at least a 3 pH unit range, preferably at least 4 pH units, and more preferably at least 5 pH units, or the thickening persists over the range of pH changes occurring during repeated use of a packaged container of the remover with reuse of an applicator which carries nail polish residue into the polish remover reservoir. The persistence of thickening occurs without the presence of a neutralizing agent (e.g., neutralizing agents as described in Helioff et al., supra and Day, supra) or pH buffer (though such neutralizers or buffers may be present) Indication that a thickener is "effective without neutralization" means that the thickening is effective without the presence of a neutralizing agent (e.g., neutralizing agents as described in Helioff et al., supra and Day, supra) or pH buffer (though such neutralizers or buffers may be present) under conditions where the thickeners described in Helioff et al. and Day would not retain adequate thickening in the absence of the neutralizers, e.g., as described therein, or effective pH buffering. Preferably the thickener is "effective in the absence of a neutralizer" over a range of at least 3 pH units, more preferably at least 4 pH units, and still more preferably at least 5 pH units.

In another aspect, the invention provides a nail polish-lacquer removing composition which includes from 51% to 99.9% of GBL, preferably from 70% to 99.9%, more preferably from 80% to 99.9% and at least one thickening agent which is present in an amount effective to produce an absolute kinematic viscosity at 20° C. of from 250 to 10,000 cp, preferably from 1000 to 10,000, more preferably from 2000 to 8,000. The thickening agent is pH stable, thus can withstand changes in pH in the LNPR preferably at least between pH 5 and 9, more preferably between pH 4 and 9, or 5 and 10, or 4 and 10 while maintaining thickening as specified.

In a related aspect, the invention provides a nail polish-lacquer removing composition which includes from 51% to 99.9% of GBL, preferably from 70% to 99.9%, more preferably from 80% to 99.9% and at least one thickening agent which is present in an amount effective to produce an absolute kinematic viscosity at 20° C. of from 250 to 10,000 cp, preferably from 1000 to 10,000, more preferably from 2000 to 8,000. The thickening agent is not neutralized crosslinked maleic anhydride-alkyl vinyl ether copolymer gel (e.g., not neutralized crosslinked maleic anhydride-$C_1$–$C_4$ alkyl vinyl ether copolymer gel) or a neutralized acrylic acid polymer (e.g., neutralized with a neutralizer containing N,N,N',N'-tetrakis (2-hydroxypropyl) ethylaminediamine and 2-ethyl-N-(2-ethylhexyl-1-hexamine). Preferably the thickening agent can withstand changes in pH in the LNPR at least between pH 5 and 9, more preferably between pH 4 and 9, or 5 and 10, or 4 and 10.

The compositions of the above aspects can also optionally include a humectant/diluent. A humectant/diluent is preferably present in an amount sufficient to enhance moisture retention in a surface to which the composition is applied, but not so high as to prevent the composition from being effective to remove nail polish, usually up 20% by weight of the composition. An acceptable maximum for a humectant/diluent will depend, in large part, on the selection of solvent compounds and the effects of the humectant/diluent or other components on the solvent activity, and can be readily adjusted to an appropriate level.

Independently, the composition can optionally contain an emollient, which preferably is present in an amount sufficient to enhance moistening of a surface, e.g., skin, with which the composition comes into contact, usually up to 10% by weight. An emollient should not be present in such a large concentration as to prevent the composition from functioning as a nail polish remover. Also preferably an emollient is not present in such a large concentration as to leave an undesirable coating on skin or nail after the composition is wiped away.

In the present invention, a solvent thickener which is combined with GBL serves at least two distinct functions. First, the thickener reduces solvent "runniness", thereby helping localize the LNPR on the nail. In fact, when a small dip-applicator device such as a brush or hollow stick applicator is used to transfer the thickened LNPR onto a nail, it has been found that as little as 10–50 microliters of the thickened GBL-based LNPR can be used to fully coat a nail and remove the nail lacquer. Second, when the LNPR is packaged in a narrow-necked container (e.g., a container having approximately a 4 mm–10 mm diameter opening) the presence of thickener helps the composition form an airlock in the container, reducing or preferably blocking the outflow of LNPR when the container is tipped onto its side or inverted. This feature helps to control misuse of the GBL-containing composition, e.g., helps to prevent a child from ingesting the LNPR, or spilling the LNPR and contacting his eyes, causing eye irritation. A substantially pH-insensitive of pH stable thickener (e.g., a thickener effective over a pH range as indicated) is preferably used so that an elevated viscosity can be maintained, even as the pH of the remover may substantially change over the lifetime of the product. For example, a brush applicator used with the LNPR, and which carries contaminants from lacquer-coated nails back into the LNPR container may cause an upward or downward pH change over a pH range of at least 5–9.

The GBL-containing compositions of the invention can also be supplemented with other types of solvent compounds, i.e., co-solvents, such as a propylene glycol-derivative solvent consisting of at least one compound which is a propylene glycol ether, a dipropylene glycol ether, a propylene glycol ether ester, or a dipropylene glycol ether ester. In preferred embodiments, propylene glycol derivative co-solvents include at least one of the exemplary compounds: propylene glycol methyl ether (PM; 1-methoxy-2-propanol, CAS No. 107-98-2), propylene glycol methyl ether acetate (PMA; 1-methoxy-2-propanol acetate, CAS No. 108-65-6), dipropylene glycol monomethyl ether (DPM; CAS No. 34590-94-8), dipropylene glycol methyl ether acetate (DPMA; CAS No. 88917-22-0), propylene glycol ethyl ether (PE; CAS No. 52125-53-8), propylene glycol ethyl ether acetate (PEA; CAS No. 98516-30-4), propylene glycol n-propyl ether (PNP; CAS No. 1569-01-3), propylene glycol t-butyl ether (PTB; CAS No. 57018-52-7), propylene glycol n-butyl ether (PNB; CAS No. 5131-66-8), and dipropylene glycol n-propyl ether (DPNP, CAS No. 29911-27-1).

As indicated above and further described below, the compositions may contain one or more other solvents, i.e., co-solvents. These other solvents may provide a variety of functions depending on the specific solvent chosen. For example, the co-solvent may function as one or more of diluent, humectant, active co-solvent, solubilizing agent for another component (e.g., a thickening agent). Preferred examples of such co-solvents include propylene glycol, lower alcohols (generally 1,2,3, or 4 carbon atoms, e.g., ethanol and isopropanol), along with others described herein. While their use may introduce some level of skin irritation, the conventional nail polish remover solvents, acetone and ethyl acetate can also be used as co-solvents if desired, e.g., to provide a highly active secondary solvent. Preferably, if used, the acetone and/or ethyl acetate is used at a low percentage, e.g., preferably equal to or less than 30%, and more preferably equal to or less than 20% or 10% or 5%.

The thickening agent is preferably present in the composition in an amount sufficient to allow the composition to provide a layer thicker than a mere liquid film layer when applied to a fingernail or toenail. A variety of different thickeners may beneficially be used, and a combination of thickeners may also be used if desired. In order to provide appropriate thickening characteristics, preferably the thickening agent or agents is present in an amount from 0.1% to 5% by weight, more preferably from 0.2% to 3%, still more preferably from 0.2% to 1%, of the composition. Preferably, a thickening agent is a cellulose derivative, a natural gum, an inorganic thickener, or a synthetic homopolymer or copolymer having from 1 to 30 carbon atoms per monomer unit. Preferred examples of cellulose derivatives include hydroxycellulose, hydroxyalkylcellulose, and carboxymethylcelluose, more preferably hydroxyethylcellulose, hydroxypropylcellulose, and hydroxypropylmethylcellulose. Preferred examples of synthetic homopolymers or copolymers are polyacrylic acid esters, polymethacrylic acid esters, polyvinylacetate, and polyvinylpyrrolidone. Preferred examples of natural gums are acacia, alginate, carrageenan, guar, karaya, pectin, tragacanth, and xanthan. Preferred examples of inorganic thickeners are silicas and clays.

As indicated above, the composition may optionally contain at least one humectant/diluent. Preferred examples of suitable humectants/diluents include water, glycerol, propylene glycol, 1,3-butylene glycol and its isomers, sorbitol and combinations thereof.

Also as indicated above, independently the composition may optionally contain at least one emollient. Preferred examples of such emollients include fatty acid esters, mineral oil, silicone oil, lanolin, lanolin derivatives and combinations thereof.

As described above, use of the propylene glycol derivative co-solvents provides certain advantages over other commonly used solvents in LNPRs such as acetone and ethyl acetate. For example, the nail polish-lacquer removing composition, upon removal, allows the fingernails and toenails to remain substantially free of any sticky residue, without addition of any electrolyte to the composition. Further, the vapors from the propylene glycol derivative co-solvent, as well as from the composition as a whole are preferably substantially non-irritating to the eyes. Also, the propylene glycol derivative co-solvent, and preferably the GBL-containing composition as a whole, is substantially non-irritating and non-sensitizing to the skin surrounding fingernails and toenails when used to remove nail polish-lacquer. The latter in vivo findings are important because erythema is a significant skin problem associated with the use of acetone-based remover products. Regardless of whether a humectant and/or an emollient were present, PM and PMA as co-solvents were much gentler to the skin than acetone, causing no visible irritation or reddening In the context of the effect of nail polish removers on human skin, the terms "non-irritating" and "non-sensitizing" mean that the solvent or composition referenced causes visibly less skin irritation, e.g., skin reddening or erythema, than acetone or ethyl acetate on equal exposure under conditions where acetone or ethyl acetate cause visible skin changes (e.g., initial whitening and drying, and subsequent skin reddening). In reference to the effects of a solvent on the eyes, the term "non-irritating" means that normal exposure of the eyes to solvent vapors during the removal of nail polish does not result in any visible reddening or discomfort to the eyes or the immediately surrounding tissues.

Many of the propylene glycol derivative co-solvent compounds have pronounced ether and ester-type odors. If desired, those solvent odors can be masked, such as by using any one of a number of top note fragrances (e.g., citrus, cherry and other fruit fragrances), which have been successfully used as maskers of these such ether and ester odors in other applications. Thus, such a fragrance may also be included in the composition.

While the thickened, GBL-containing solvent-based nail polish remover composition provides advantages as briefly described above, such as being non-irritating and non-sensitizing, and further can be more convenient to use due to its low volatility and consequent slow evaporation, in some cases it may be desired to add a more volatile solvent component to a GBL-based polish remover. For example, it may be desired to add a more volatile solvent as a co-solvent in order to provide a more active total solvent. Therefore, even a solvent such as acetone or ethyl acetate, can be added to the composition, but in such preparations, the co-solvent component is present at levels substantially below those which would be used if the co-solvent were the principal solvent component in a nail polish remover. Thus, preferably the co-solvent component or components is present at, or less than the percentage which would be used if the co-solvent were the principal solvent in a nail polish remover. Preferably, the co-solvent is present at 40% or less by weight of the composition, more preferably 30% or less, still more preferably 20% or less, and most preferably 10% or 5% or less. Preferably, the addition of one or more co-solvent compounds alongside of GBL does not cause the composition to become irritating or sensitizing to the skin or the vapors irritating to the eyes of a user. Preferably the addition of such a solvent component increases the solvent activity of the composition toward a nail polish.

In another aspect, the invention provides a nail polish-lacquer removing composition which includes butyrolactone solvent and/or a propylene glycol derivative solvent, where the butyrolactone and propylene glycol derivative solvents together are 51–99.9% by weight, preferably 70–99.9%, more preferably 80–99.9%, of the total nail polish-lacquer removing composition. Preferably both butyrolactone and a propylene glycol derivative solvent are present. Preferably the butyrolactone concentration is greater than the propylene glycol derivative solvent concentration.

As described for compositions above, other co-solvents may also be present if desired.

Additional embodiments are as described for nail polish-lacquer removing compositions described above and in the following Detailed Description.

In a related aspect, the invention provides a method of removing a nail polish-lacquer coating from a fingernail or toenail without causing irritation of the skin surrounding the nail using a nail polish removing composition as described above. The nail polish-lacquer can be a pigmented lacquer, a glitter-containing lacquer, or some other novelty lacquer which may be produced by the cosmetics industry from time to time. The method includes the steps of:

(i) applying the nail polish-lacquer remover composition described above to the coating on the fingernail or toenail;

(ii) allowing the coated fingernail or toenail and the remover composition to remain in contact for a time sufficient to loosen the coating from the fingernail or toenail, and (iii) separating and removing the coating and the remover composition from the fingernail or toenail.

The steps may be repeated as needed to accomplish full removal of the coating from the nail.

As previously discussed, application of the composition may preferably be accomplished using any convenient dipping-type applicator such as a brush or swab-type applicator, for example. It is preferred that the applicator is integrated into the lid of the container holding the LNPR. For example, a small applicator brush on a shaft can be attached to a screw cap lid, and extend downward into the LNPR, much like a nail polish applicator brush extends downward into a bottle of nail polish.

The time required for softening and loosening a nail lacquer coating in vivo varies with the choice of solvent or solvents described herein, and the presence or absence of any co-solvent, diluent, humectant, emollient and the like, as well as the particular type of nail polish. Typically however, waiting about 15 seconds after application before wiping the coating and remover composition from the nail is adequate. The time range presently considered practical for this delay between application and removal is between approximately 10 seconds and 2 minutes. A paper tissue or absorbent paper towel or an absorbent fiber ball, such as a cotton ball, may be conveniently employed for wiping away, i.e., separating and removing, the nail polish and remover composition from the fingernail or toenail.

In preferred embodiments, the composition is as described in embodiments of aspects above, e.g., including preferred packaging in a narrow-necked bottle.

The examples described below will illustrate and compare the in vitro effectiveness of GBL and a variety of propylene glycol-derivative co-solvents in softening and releasing a conventional nail polish.

In connection with the use of the present nail polish lacquer-removing compositions, the term "a time sufficient to loosen the coating from the fingernail or toenail" means a time sufficient so that a substantial portion of the coating under remover composition is sufficiently loosened so that it can be wiped away, but not so long that the remover composition dries sufficiently that the remover composition cannot be fully wiped away. The phrase "loosen the coating from the fingernail or toenail" refers to a process of partially or fully softening or dissolving the nail polish coating, or loosening the adhesion of the coating to the nail, or combinations of those effects. The phrase "separating and removing the coating and the remover composition" refers to a process of removing at least a portion of the nail polish, e.g., by wiping away with an absorbent fiber ball. Highly preferably, at least most of the nail polish from the nail being treated is removed in a single treatment, preferably such that only a clean-up treatment or no further polish removal treatment is needed.

In a further aspect, the invention provides a method of treating a granular suspension of between 0.1% and 5% by weight hydroxypropylcellulose, preferably between 0.25% and 1%, contained in a liquid comprising between 51% and 99.9% by weight butyrolactone, to produce a smooth-textured thickened solution. The method involves removing a sufficient proportion of granular material from the suspension to provide the smooth-textured thickened solution. The granular material can be removed in a variety of different ways, including, for example, shearing, filtering, or centrifuging the suspension, or using two or more of those techniques in combination. Thus, in preferred embodiments, the suspension is sheared and filtered; the suspension is centrifuged; the suspension is sheared and centrifuged; the suspension is filtered.

In the context of this invention, the term "propylene glycol-derivative solvent or co-solvent" refers to a compound or mixture of compounds which is liquid at room temperature and in which the compound or compounds can be viewed as chemical derivatives of propylene glycol with the addition or substitution of one or more substituent groups, generally substituting on the hydroxyl groups. The substituent groups do not cause the solvent compound to become irritating to the skin or toxic. In order to provide sufficient volatility, the solvent compounds are limited to those having one or two propylene glycol monomer units. A limited amount of larger molecules, such as tripropylene glycol methyl ether or other derivative could also be used in combination. The substituents are preferably hydrocarbon or carboxylate groups having 1,2,3, or 4 carbon atoms and/or, more preferably 1 to 3, and most preferably 1 to 2 carbon atoms, thus forming ethers and/or esters. Preferably the hydrocarbon group is an alkyl group. As indicated above, preferably a derivative is an alkyl ether or alkyl ether ester derivative In connection with the concentrations of the various components in the described compositions, the ranges of percentages include the end points. For example, a range of 70 to 99.9 weight %, or 70–99.9 weight %, for a component A, means that the compositions can include 70% or 90% or any other concentration of component A within those endpoints, but including the endpoints. Also in this context, a "wt. %" or "weight %" or "weight percent" or "percent by weight" refers to the conventional calculation of weight percent, that is:

wt. % of component $A$=[(weight of component $A$ in composition) ÷(total weight of composition)]×100.

The term "thickening agent" refers to a compound or combination of compounds which acts to increase the viscosity of a liquid solution or suspension. Preferably a thickening agent is not present in such a large amount as to result in solidification of the composition. It is highly desirable that the composition remain able to be smoothly applied on a nail and/or to flow slowly. Thus, the presence of a thickening agent preferably results in partial thickening or partial gelling, resulting in a viscous liquid.

The term "humectant/diluent" as commonly used in connection with skin care products and as used herein, refers to a compound or compounds which acts to enhance moistening or moisture retention, e.g., by human skin and tissue, and/or dilute the solvent in a composition as described. Preferably, one compound performs both functions. While usually one compound will be provided as a "humectant/diluent", more than one compound can be utilized in combination, and such multiple compounds is included in the term "humectant/diluent".

The term "emollient" is used in its usual skin care sense, referring to a material which promotes softening of a material to which it is applied, e.g., human skin. While usually one compound would be used in the present compositions as an emollient, more than one compound can be used, and such multiple compounds are included in the term "emollient". Those skilled in the art are familiar with a variety of compounds suitable for this purpose and their appropriate usage. The terms "narrow neck(ed)" refers to the upper portion, including the container opening, of a container such as a bottle used to hold the nail polish remover, and more specifically to the inner diameter or width of the container opening which provides access to the liquid contents. Preferably, this diameter is between 3 mm and 10 mm (endpoints included), more preferably between 4 mm and 10 mm or 4 mm and 7 mm.

In connection with flow of contents from a narrow-necked bottle or container, the term "retard" or "reducing" indicates that the outflow from a normally filled container or bottle at normal room temperatures is much slower than from a bottle of similar capacity and similar internal dimension in the lower portion of the bottle but which does not have an opening or neck which retards flow. Preferably the outflow is not a continuous stream when the bottle or container is tipped at 90 degrees or inverted. Preferably, the outflow of ½ of the contents of a narrow-necked bottle requires at least twice as long (2×), more preferably at least 5 times as long (5×), still more preferably at least 10 times as long (10×) as the outflow of ½ of the same volume from a straight-sided glass beaker. Preferably the outflow stops completely prior to the outflow of ½ or ¼ of the contents of the narrow-necked container or bottle.

The term "bittering agent" refers to a chemical which, when added to a LNPR composition, has the effect of discouraging or interfering with its ingestion, particularly its accidental ingestion by children, by providing an unpleasant, often bitter taste. One preferred bittering agent is denatonium benzoate (also known as Bitrix®) which can be added to the LNPR at a concentration of approximately 0.01%–0.02% by weight.

In the context of the present compositions, the term "microliter quantities" means a volume between 1 and 100 microliters, preferably between 5 and 70 microliters, and more preferably between 8 and 60 microliters. In preferred embodiments, a volume averaging not more than 5, 10, 20, 30, 40, 50, 60, 70, or 100 microliters is applied to a nail, where the standard deviation for replicate applications is not more than 0.5. Thus, in the present methods, such quantities of the described nail polish-lacquer removing compositions can conveniently be applied to a nail, so that the applied volume does not exceed an upper limit as just described but is preferably sufficient to coat the entire nail. The methods and kits thus provide controlled application of small volumes of remover compositions, typically without the waste associated with use of disposable absorbent materials, such as disposable swabs or absorbent fiber balls.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other embodiments are within the scope of the invention as described by the following Detailed Description of the Preferred Embodiments and by the claims.

DETAILED DESCRIPTION OF THE PREFERRED EMBODIMENTS

As described in the Summary above, the present invention provides a thickened LNPR (liquid nail polish remover) which is based upon the solvent, gamma butyrolactone (GBL) and/or propylene glycol derivative solvents which is not irritating or sensitizing to the skin around the fingernail or toenail of a user. In contrast to acetone and ethyl acetate-based removers, GBL (on a propylene glycol derivative solvent) is substantially non-volatile, and for reasons which are still unclear, causes little drying of the skin around the nail, and no skin irritation or sensitization upon repeated application, even in the absence of any humectant or emollient. The GBL nail lacquer remover is only moderately toxic upon ingestion, and has no vapor inhalation hazard. The likelihood of accidental ingestion (e.g., by children) is reduced by adding a bittering agent such as denatonium benzoate, and a solvent thickener which, if the LNPR is packaged in a narrow-necked container, can retard or block the flow of LNPR from the container if the container is inverted or tipped on its side. GBL is water-miscible, biodegradable, and its vapors cause no irritation of the eyes. Even in the absence of an electrolyte, the remover composition leaves no gummy or sticky residue after solvent evaporation, or after wiping of the nail polish/solvent residue from the nail. Furthermore, the remover composition is especially useful for loosening and removing hard-to-remove so-called "glitter" nail lacquers which contain suspended flecks of solvent-inert material such as polyester film.

Accordingly, a thickened nail polish-lacquer removing composition is provided, having a smooth, substantially non-granular consistency. The composition is substantially non-irritating and non-sensitizing to the skin surrounding the fingernails and toenails. Upon drying, the residue of the lacquer-removing composition is water-soluble. In preferred embodiments of the nail polish remover composition described above, the nail polish removing composition includes:

(i) from 51% to 99.9%, or preferably 70% to 99.9% by weight of the organic solvent, GBL;

(ii) from 0.1% to 5% by weight of at least one water-soluble thickening agent capable of functioning in the absence of a neutralizing agent such as hydroxypropylcellulose (e.g., KLUCEL® H or KLUCEL®G, a so-called "high molecular weight hydroxypropylcellulose" manufactured by Hercules, Inc., Aqualon Division, Wilmington, Del.), and which is present in an amount effective to produce an absolute kinematic viscosity or a Brookfield viscosity at 20° C. of from 250–10,000 cp;

(iii) optionally, from 0% to 49% by weight of a co-solvent which is selected from the group consisting of propylene glycol ethers such as propylene glycol methyl ether (PM), dipropylene glycol ethers such as dipropylene glycol methyl ether (DPM), propylene glycol ether esters such as propylene glycol methyl ether acetate (PMA), dipropylene glycol ether esters such as dipropylene glycol methyl ether acetate (DPMA), and mixtures thereof;

(iv) optionally, from 0% to approximately 20% by weight of a humectant/diluent which is selected from the group consisting of water, glycerol, propylene glycol, 1,3-butylene glycol and its isomers, sorbitol and combinations thereof;

(v) optionally, from 0% to approximately 10% by weight of an emollient which is selected from the group consisting of fatty acid esters, mineral oil, silicone oil, lanolin, lanolin derivatives and combinations thereof.

Within the above composition ranges specified for compositions of this invention, particularly active and effective nail polish remover formulations can include approximately 51% to 99.9% by weight of GBL, varying proportions of PM, PMA or solvent mixtures thereof, and 0.1% to 5.0% of a water-soluble thickening agent such as hydroxypropylcellulose. One easily formulated active remover contains approximately 99%–99.5% by weight GBL and 0.5% to 1.0% of KLUCEL®H.

Also as indicated above, optionally, up to approximately 10% by weight of an emollient can also be included in the nail polish remover. Conventional emollients used in acetone and ethyl acetate removers include fatty acid esters, mineral oil, silicone oil, lanolin, lanolin derivatives and combinations thereof. However, the solvents used in the present invention are considerably less irritating and depleting of skin oils than either acetone or ethyl acetate, so that addition of an emollient to the formulation may be considered an enhancing feature or option, rather than a necessity.

In practicing the present invention, the nail polish lacquer remover composition described above (which can be conveniently provided in a 25–100 ml bottle (or 1–3 fluid ounce) bottle having a small removable brush or swab applicator or a sponge applicator), is applied sparingly to the nail. Typically only 10–50 microliters of thickened liquid need be brushed or otherwise applied to the fingernail or toenail. Generally, 10–30 seconds, and typically about 15 seconds are allowed for the remover to soften and dissolve typical polish-lacquers before wiping away the residues with a paper tissue or cotton, for example. As much as 60–120 seconds contact time with the remover composition may be desirable when stripping off hard to dissolve nail polish-lacquers such as glitter polishes (see below). The process may be repeated if any polish-lacquer remains on the surface of the nail or around its perimeter. A user applying the composition to his or her nails will find that it is easy to precisely control coverage of individual nails using the thickened liquid and a small applicator. Heavier or lighter application of the remover onto the nail may be appropriate depending upon the particular formulation of nail polish and its ease in being solubilized by the solvent-containing composition.

Presently invented nail polish lacquer removers are unusual in their performance in vivo when compared to acetone and ethyl acetate-based removers. For example, while the GBL solvent is only slightly volatile (vapor pressure=0.2 mm Hg at 20° C. versus 20 mm Hg for water), and will persist on the nail for as long as desired, ethyl acetate and acetone are highly volatile (80 mm and 200 mm Hg respectively at 20° C.) and must be replenished frequently when removing a stubborn nail polish. All of these solvents are miscible with water and have the ability to mobilize or remove fats and oils from hard surfaces. Indeed, GBL and the propylene glycol-derivative co-solvents are sold industrially as oil-thinning solvents. Yet when GBL and the co-solvents PM, PMA were applied to fingernails and the surrounding skin alongside of acetone and ethyl acetate for between 15 and 60 seconds and then removed, the GBL, PM and PMA-containing removers were visibly gentler to the skin than comparable acetone and ethyl acetate treatments. While a single acetone treatment caused immediately and dramatic skin and cuticle surface whitening and drying (moisture and skin oil removal), GBL, PM and PMA treatment produced little effect. While three to four-fold successive acetone applications to the fingernail caused significant skin reddening around the fingernails (erythema), similar applications of GBL, PM and PMA treatments caused no such skin reddening.

The latter in vivo findings are important because erythema is a significant skin problem associated with acetone-based remover products. Regardless of whether a humectant and/or an emollient were present, GBL, PM and PMA were much gentler to the skin than acetone, causing no irritation or reddening. Concerning exposure of the eyes to solvent vapors, acetone has proven to be a significant eye irritant during nail polish removal. This may be a result of the very volatile nature of acetone, the significant exposure period and the proximity of the eyes to the fingernails during nail polish removal. By contrast, GBL, PM and PMA solvent vapors caused no eye irritation or eye discomfort during in vivo nail polish removal. Given the irritancy of conventional acetone-based removers to skin and eyes, and given a generally health-conscious public, it is indeed remarkable that acetone-based removers have continued to be formulated, and widely used.

While it was observed that the PM and PMA solvents used alone were somewhat slower to dissolve dried nail lacquers than acetone and acetone-ethyl acetate removers, GBL solvent was almost as aggressive as acetone. For example, while 100% acetone allowed a doubling coating thickness of dried lacquer nail polish to be wiped away cleanly within 6–8 seconds following solvent contact (depending upon lacquer thickness and age of the dried lacquer) 100% GBL required approximately 9–11 seconds contact time before the lacquer polish could be cleanly removed. However, compared to acetone, Applicant found that the persistence of GBL-containing coatings owing to their much lower volatility, allowed stubborn dried nail polishes such as glitter polishes (see below) to be removed much more easily. In fact, one coating of GBL-based LNPR when allowed to sit 2 minutes on a glitter polish allowed the polish to be wiped off cleanly or rinsed away with water, whereas acetone remover evaporated to dryness within approximately 10 seconds without even softening the glitter polish.

To offset any apparent difference in efficacy between the GBL-based and acetone-based removers, Applicant found that increasing the solvent coating thickness on the fingernail was helpful in facilitating nail polish removal. Various solvent thickeners were tested for their abilities to dissolve in GBL. For GBL (with or without co-solvents), 0.25%–1.0% by weight hydroxypropylcellulose (such as KLUCEL®H or KLUCEL®G, obtained from Hercules, Inc., Aqualon Division, Wilmington, Del.) was useful.

In addition, as pointed out in the Summary, if desired the solvent can be "spiked" by adding a highly volatile co-solvent component such as acetone or ethyl acetate, although other solvents can also be used as additional components. However, the highly volatile co-solvent does not constitute the principal active solvent for loosening or removing a nail polish. Thus, the co-solvent component is a secondary solvent component.

As stated earlier, the presently invented GBL-based LNPR compositions demonstrated remarkable efficacy in loosening and removing the class of nail lacquers known as "glitter" enamels or polishes. Typically, the glitter-type products are distinguished from normal nail lacquers by the presence of an abundance of small polyester flakes or "flecks" which are light-reflective and/or light-defracting, producing a tinsel-like effect in the polish. Polyester flecks are solvent-resistant, and together with the clear lacquer vehicle, have proven to resist both acetone and ethyl acetate-based nail polish removers.

For example, one coat of a typical glitter lacquer (Jane brand, product no. 23 VOLTAGE™, produced by Sassaby Cosmetics, Inc., Cardiff by the Sea, Calif.) was applied to a glass plate surface and air-dried overnight. Approximately 50 seconds of continuous rubbing were required for an acetone-based remover to loosen and remove the coating (using a solvent-saturated Q-tip swab). An ethyl acetate-based remover required 65–70 seconds to achieve the same result. These time periods were essentially 5–10-fold longer than the time required to remove conventional pigmented nail polishes. As a result of the extended time duration, and the highly volatile nature of acetone and ethyl acetate, it was necessary to apply these removers repeatedly to the glitter coating to achieve its removal. By comparison, only a single application of a formulation of the present invention (containing 99.5% by weight GBL and 0.5% KLUCEL®H) was required because the GBL is much less volatile than either acetone or ethyl acetate. Shortened solvent contact times (as little as 30 seconds) were required for the GBL-based remover to loosen the glitter coating, compared to approximately 60 seconds for ethyl acetate-based remover. While conventional acetone and ethyl acetate removers evaporate in less than 10 seconds, GBL can persist for several minutes on the nail. Both the presence of a thickener (which allows a heavier coating of remover to be applied to the nail), and the lower volatility of the GBL (compared to acetone), contribute to its persistence.

In the interest of further describing the present invention, the most abundant organic solvent molecular species used in the preferred LNPR compositions of the present invention, is gamma-butyrolactone ($C_4H_6O_2$) or GBL (CAS#96-48-0). It has a remarkably low volatility and high flash temperature (209° F.), considering its low molecular weight (86.1). This allows safe handling and shipping of GBL-based LNPR products. GBL is miscible with water, allowing convenient wash-off of residues on the nail. The optional propylene glycol-derivative co-solvent molecule used in embodiments of the nail polish lacquer removing composition of the present invention, contains between 4 and 9 carbon atoms and between 2 and 4 oxygen atoms. Thus, at one limit, PM contains 4 carbon atoms and 2 oxygen atoms, and at the other limit DPMA contains 9 carbon atoms and 4 oxygen atoms. The vapor pressure of the propylene glycol solvent or co-solvent is at least 0.05 mm Hg, and preferably greater than 0.5 mm Hg at 20° C. For example, PM and PMA which are preferred co-solvents have vapor pressures, respectively, of 8.1 and 3.8 mm Hg at 20° C. While these solvents may be combined with other liquids including diluents and/or humectants and/or emollients, the concentration of organic solvent(s) ranges from approximately 70% to 99.9% by weight and preferably from approximately 79% to 99.5% by weight.

The presence of a thickening agent is also highly preferred for the functioning of the present invention. First, the thickener allows a submersible dipping-type applicator, such as a brush or sponge-type applicator, to be used to transfer an adequate amount (e.g., approximately 10–50 microliters) of the viscous or semi-gelled liquid remover from the storage bottle to the nail. The applicator then allows spreading of the remover over the nail surface. The thickener also helps in the economy of use of the remover by localizing and maintaining an adequately thick coating of the remover on the nail and cuticle surface where it is needed for softening and dissolving the nail polish. Especially if any volatile co-solvent is added, any solvent spreading promotes rapid solvent evaporation and loss of efficacy in dissolving the nail polish. The concentration and type of thickener are selected to establish a viscosity which allows the above-described coatings to be formed on nails. Empirically, the absolute kinematic viscosity (measured by Canon-Fenske ASTM size 500 viscometer at 20° C.) is preferably in the range of between 250 and 10,000 centipoise (cp), preferably between 100 and 10,000 cp. A glycerin viscosity standard was used (1,490 cp at 20° C.).

One of the benefits of the present invention concerns the solution of the problem addressed in Miner, U.S. Pat. No. 5,543,085, which was concerned with eliminating gummy and sticky residues of traditional thickeners (e.g., acrylic acid polymers and hydroxypropylcellulose). These residues, which appear as the solvent evaporates from acetone-based nail polish removers, cause the fibers in cotton ball applicators to adhere to nails and fingers. Miner relies upon the addition of an electrolyte to change the gummy characteristic of such residues produced following acetone and ethyl acetate solvent treatment of nail polish-lacquer. In the present invention, it has been discovered that gummy and sticky thickener residues need not be formed in the first place, if alternative solvents as described are selected. This is true even when one or more of the traditional thickening agents of Miner (e.g., hydroxypropylcellulose) is present in the nail polish remover formulation.

Similarly, one of the principal objects indicated in Bayless, U.S. Pat. No. 5,372,742 is concerned with replacing acetone-ethyl acetate and other solvent systems in order to eliminate their disagreeable odor, irritancy to the skin and eyes, and drying of the cuticle and nails. Bayless relies upon a non-aqueous cleaning composition based upon d-limonene, a terpene. With regard to several other ingredients which can be added to a mixture of d-limonene, ethyl lactate, and cetyl acetate, Bayless mentions the optional use of between 10% and 50% by weight of PMA. However, the function of PMA is unclear in the compositions described in the Bayless patent. In contrast, the present compositions utilize a GBL and/or a propylene glycol derivative solvent as the principal component of the composition. Furthermore, Bayless combines PMA and d-limonene (15%–60% by weight), which renders the nail polish remover unusable for the purposes of the present invention.

It is generally known that propylene glycol ether and propylene glycol ether acetate-based solvents are used as cost-effective diluents in N-methyl-2-pyrrolidone (NMP)-based commercial paint removers, industrial cleaners, grease removers, and the like. However, Applicant is unaware of any previous suggestion that:

(i) these propylene glycol-derivative solvents are effective as co-solvents which, together with GBL, provide an effective nail polish remover, (ii) GBL and these co-solvents, when combined with traditional thickeners, e.g., hydroxypropylcellulose, are free of the normal tackiness which accompanies solvent evaporation in the traditional acetone and ethyl acetate-based products, or that (iii) GBL and these co-solvents cause no skin irritation or reddening when compared with the acetone and ethyl acetate-based nail polish removers.

One of the propylene glycol ethers (PM, also known as 1-methoxy-2-propanol) is an especially effective co-solvent when combined with GBL, and when thickened with a cellulosic polymer agent, e.g., hydroxypropylcellulose, provide a very useful nail polish remover. While PM is the most volatile of the propylene glycol derivative co-solvents described in the present invention (vapor pressure=8.1 mm Hg at 20° C.), it is far less volatile than acetone or ethyl acetate, and especially when combined with GBL (vapor pressure=0.2 mm Hg at 20° C.) persists on the nail for a time sufficient to soften the most stubborn of nail lacquers (i.e., persisting for at least 1–3 minutes, depending upon the coating thickness) before evaporating. By contrast, acetone and ethyl acetate are extremely volatile causing a significant inconvenience. They persist only 5–10 seconds on the nail (10-fold less time than PM) before they must be replenished. These observations are consistent with the high vapor pressures of ethyl acetate and acetone at room temperature (approximately 80 mm and 200 mm Hg which are approximately 10 and 20-fold greater than that of PM, 8 mm Hg).

As an additional advantage, GBL as well as all of the propylene glycol ethers and propylene glycol ether acetates including the PM and PMA solvents are "environmentally friendly", in the sense that none are listed on the EPA's HAPS and SARA hazardous chemicals lists, and they are all bio-degradable. PM is especially user-friendly because it is even substantially non-irritating to the eyes. GBL has a low rating of flammability (DOT class 1), and PM has a similar flammability to ethanol and acetone (DOT class 3).

In a panel study, conducted with the cooperation of Cosmetic Coatings Corporation (Carlstadt, N.J.), users reported that a GBL-based nail polish remover containing 99.5% by weight GBL and 0.5% by weight KLUCEL®H was superior to a conventional acetone-based product because it removed nail lacquer just as rapidly as acetone but unlike acetone, was non-irritating to the skin, did not dry out the nail and cuticle and did not become sticky like acetone as it was wiped away together with dissolved nail enamel. A convenient means of applying and localizing the semi-gelled GBL-based liquid remover on the fingernail or toenail without wasting any of the remover is by nail polish brush. Accordingly, for consumer use, the thickened remover can be usefully packaged in a small container, e.g., a one ounce capacity bottle, having a screw cap closure with an integral brush-type applicator.

While GBL has almost no odor, if PM and/or other volatile propylene glycol ethers and ether-acetates are added as co-solvents, they have rather pronounced ether and ester-type odors. Any one of a number of top note fragrances (such as citrus, cherry and other fruit fragrances) can be added as maskers of these odors.

The described nail remover compositions can be readily prepared or formulated. Those familiar with the formulation of products such as skin care and other cosmetic products readily understand the procedures and significant preparation parameters involved in formulating and packaging such products as the present compositions. Preferably the components utilized for these compositions are selected to be suitable for cosmetic use.

In general, the preferred solvent components are miscible in each other and generally are also miscible with water. Thus, preparation of a solvent mixture merely involves combining and mixing those components.

Most of the specified thickeners are highly soluble or at least form stable colloids in many of the preferred propylene glycol derivative solvents, and thus can be combined with the solvent and solubilized by mixing at room temperature or at a slightly elevated temperature in order to accelerate the dissolving. Generally this would be performed at atmospheric pressure with the temperature below the boiling point of the solvent, e.g., at a temperature at least 10° C. below the boiling point for a solvent, and more preferably at least 20° C. below the boiling point. In addition, if a thickener is not soluble in a base solvent, a co-solvent can be added in which the thickener is soluble. In some cases, a humectant/diluent can act as such a co-solvent. Those skilled in the art will readily recognize suitable co-solvent/thickener selections.

Humectants commonly used in the preparation of cosmetics are generally also miscible in the propylene glycol derivative solvents, and can therefore by freely added by simple mixing with the solvent.

Emollients may be of a variety of different types, and have different properties. Those skilled in the art will recognize the appropriate methods for incorporating particular selections of emollients in the present compositions. In particular, many emollients can be incorporated by the formation of stable emulsions. Methods for forming such emulsions are well-known in the art and so are not expressly described herein.

Since GBL is as much as seven times more costly per pound than conventional remover solvents (such as acetone and ethyl acetate), the commercial success and cost-effectiveness of the GBL-based remover depends upon providing the LNPR in a small quantity (e.g., approximately ½–2 ounces), and then using it very effectively and sparingly. By comparison, acetone and ethyl acetate are commonly sold in 6–12 ounce or larger quantities. An economy of usage for GBL is achieved by providing the LNPR in a thickened form which is easily transferred without dripping or spilling, and a solvent applicator device that can repeatedly deliver microliter quantities, e.g., approximately 10–50 microliters, of the LNPR to a nail with little or no waste. One suitable applicator is a small brush attached to a bottle lid such as that currently provided with printing correction fluids and nail lacquers. Compared to the traditional saturated cotton ball used for applying conventional acetone LNPRs, a miniature brush applicator allows as little as ten microliters to be used in removing lacquer from each nail. With regard to safety, since GBL has moderate oral toxicity, the presence of a thickener in the LNPR, when combined with packaging the LNPR in a narrow-necked bottle helps to prevent product ingestion by children (the thickened product flows slowly if at all through the narrow-necked opening). A bittering agent is also preferably added to the LNPR to discourage any ingestion.

As discussed above, Helioff et al. (U.S. Pat. No. 5,024,779) describe a viscous creamy LNPR which may include GBL. To obtain a smooth texture, a polymeric thickener consisting of neutralized crosslinked maleic anhydride-alkyl vinyl ether copolymer was utilized. Although not explicitly stated by Helioff et al., it is believed that cellulose-derived thickeners (such as hydroxypropylcellulose) were found be be unsuitable because the cellulosics either fail to dissolve, or form granular rather than creamy thickened solutions in polar organic solvents such as acetone and GBL. This granular texture is acknowledged by the manufacturers of hydroxypropylcellulose (KLUCEL®: Physical and Chemical Properties; product brochure; Hercules Inc., Aqualon Division, Wilmington, Del.).

However, cellulosic thickeners have the advantage of maintaining solution viscosity over a broad pH range (at least between pH 5 and 9) while the copolymer of Helioff et al. must remain at neutral pH to maintain viscosity. In the present invention, use of a pH-insensitive thickener is desirable because the pH of the LNPR may change over the lifetime of the product as for example, the applicator brush is repeatedly returned to the LNPR container after applying LNPR to fingernails and toenails.

To allow the use of a pH-insensitive cellulosic thickener (hydroxypropylcellulose) in the present invention, a method was developed to convert KLUCEL® (after dispersal in GBL) from an unacceptable granular suspension to a creamy-smooth, thickened solution. The method utilized, which involves shearing and filtering the granular suspension, is as follows: KLUCEL® type H was dispersed into GBL liquid by propeller stirrer (1% by weight final concentration). After incubating the particle suspension for approximately 4–6 hours at 23 degrees Celcius, the liquid appeared uniform but highly granular. The suspension was transferred to a Hockmeyer blade-type high speed disperser. The disperser was run at 1500 rpm for 1 hour and finally 5000 rpm for 0.5 hours. This treatment, which would be expected to shear cellulose polymer chains and substantially reduce solution viscosity, eliminated most of the suspension's granularity while surprisingly, not significantly reducing the solution viscosity. To eliminate remaining granularity, the solution was mesh-filtered through a polyester organza cloth material. Final KLUCEL®H concentration was adjusted to between approximately 0.25%–1.0% by weight (preferably 0.25% or 0.5% by weight) by addition of GBL and/or other components constituting the LNPR. Including other viscosity grades and types of cellulosic thickeners, the overall cellulose concentration can range between 0.1% and 5% by weight. In any event, the absolute kinematic viscosity of the LNPR measured by the Brookfield or Canon-Fenske method at 20° C. is preferably between 250 cp and 10,000 cp. As indicated above, other methods for eliminating the granularity of a cellulosic thickener can involve centrifugation, e.g., centrifugation at approximately 5,000×g. As recognized by those skilled in the art, the time and/or speed of centrifugation can be readily adjusted to provide beneficial or optimal separation.

In addition, it was observed that lower molecular weight thickener, e.g., KLUCEL®G, resulted in significantly less or no granularity or initial dissolving approximately twice as much KLUCEL®G (avg, molecular mass=330 kD) was required to produce equivalent thickening as compared to KLUCEL®H (avg. molecular mass=1.15 Mda). Thus, suitable selection of the thickener may eliminate the need to eliminate granularity.

The effectiveness of the presently invented LNPR derives from certain chemical and physical properties of GBL which distinguish it from nearly all other nail polish remover solvents with the possible exception of N-methylpyrrolidone (abbreviated NMP). GBL and NMP are highly aggressive paint-dissolving solvents which, unlike acetone, ethyl acetate, methylene chloride and the like, have unusually low vapor pressures and volatilities. Applicant has found that the combination of solvent potency and low volatility, not only allows GBL to rapidly soften and dissolve nail lacquers, but then allows the lacquer residue to be wiped away cleanly without leaving a sticky lacquer residue. By contrast, the high volatility of acetone, ethyl acetate and many other solvents leads to premature solvent evaporation, resulting in a sticky nail lacquer residue being left on the nail. Then, cotton applicator fibers inconveniently adhere to such sticky residues.

According to the present invention, GBL is preferred over NMP, acetone and other solvents as a LNPR solvent for other reasons as well; Whereas NMP and acetone are moderate skin irritants, causing redness, cracking and blistering of the skin around the nails after repeated contact, GBL has been found to cause no such skin irritation after repeated application (in spite of it causing eye irritation). Aside from the cost advantage of acetone, considering the irritancy of acetone and its inconvenience of use due to its extreme volatility, it is surprising that acetone has been the preferred LNPR for so many decades. There are also environmental issues related to the use and disposal of many other organic solvents. For example, under the U.S. Environmental Protection Agency, NMP is a SARA Title III Section 313-listed polluting solvent. GBL, on the other hand, is environmentally "friendly" and SARA-unlisted, being readily hydrolyzed to hydroxybutyric acid, a natural product found in human urine.

As a LNPR solvent, GBL is also preferred over the propylene glycol ethers and propylene glycol ether ester solvents described recently by Applicant in co-pending U.S. patent application Ser. No. 09/144,189. This is because GBL is more potent and acts considerably faster to soften and remove conventional nail lacquers, particularly lacquers which have dried and hardened on the nail for between several days and one week. In this regard, experiments indicate that a single application of GBL-based LNPR (90%–99.5% by weight GBL plus thickener) can dissolve a hardened nail lacquer at least twice as rapidly as PM (and approximately the same speed as continuous acetone treatment).

In spite of the many advantageous properties of GBL, Applicant believes that several problems have prevented commercialization of a GBL-based LNPR. Identifying and solving these problems constitute an important part of the present invention. The first obstacle to using GBL as a major component in a LNPR formulation is cost. Although GBL was mentioned in Helioff et al. and Day as a possible chemically effective LNPR solvent, its current cost of approximately $2.00 per pound has largely ruled it out as a commercially competitive LNPR ingredient, when compared to acetone at $0.28 per pound, and ethyl acetate at $0.35–0.40 per pound (bulk prices). Second, the thickening systems for a GBL-based LNPR as described by Helioff et al. and Day, become unworkable if a significant pH change occurs in the solvent, i.e., viscosity would be lost. Third, the formulation of Helioff et al., yields a water-insoluble coating on the nail, requiring soap and water for its removal. Fourth, GBL has been identified as a potential health hazard, inducing reversible coma if orally ingested in substantial quantity (gamma butyrolactone-Material Safety Data Sheet, 1998, Arco Chemical Company, Newtown Square, Pa.). As a result of this child-safety hazard, Applicant was advised by the Arco Chemical Company, that GBL is not favored for use in a consumer product.

Several practical and cost-effective remedies have now been found for the above GBL-related problems. These remedies, in brief, involve:

(a) Providing a re-usable microapplicator which facilitates sparing application of the LNPR to individual nails, thereby reducing the amount of LNPR and the cost of GBL solvent required for removing polish from each nail. With the applicator described, a container has been tested with as little as one ounce of GBL-based LNPR which is adequate for removing nail lacquer from a set of ten fingernails on 50–100 separate occasions, using only between 10 and 50 microliters of the LNPR per nail.

(b) Utilizing a narrow-necked container with a limited capacity, e.g., not more than 25, 30, 50, 60, 80, or 100 ml. (or 1, 2, or 3 fluid ounces).

(c) Modifying the composition of a prior art GBL-containing LNPR by employing a pH-insensitive thickener. This thickener allows repeated use of the microapplicator (see A above) without danger of viscosity loss, even when a pH change occurs in the LNPR (e.g., with entry of contaminants into the LNPR via the microapplicator). Unlike the thickener of Helioff et al., the selected thickener is water-soluble to allow convenient water rinsing of the nails (no soap required) following nail polish removal.

(d) Introducing a bittering agent such as Bitrix® which, together with the thickener, reduces the risk of GBL ingestion by children. Compared with commercially packaged quantities of conventional LNPRs (6–12 ounces), the reduced quantity of GBL used in a packaged LNPR of the present invention (typically 1 ounce) also reduces the overall toxicity risk to children.

The following description is intended to provide a more detailed explanation of these remedies. Item (a) is discussed first. In the absence of any information on how the creamy nail polish of Helioff et al., U.S. Pat. No. 5,024,779 is to be applied to the nail, the conventional method of applying a LNPR and removing the lacquer is assumed, i.e., by use of a cotton ball. In this case, a quantity of approximately 1–2 grams of LNPR is instilled into a cotton ball or wad of toilet paper, which is then used to cleanse one or two nails at a time. In the process of removing lacquer from ten fingernails, between five and ten grams of LNPR may be utilized. Based upon the current price of chemicals, ten grams of a GBL-based remover @ $2.00 per pound would cost approximately 4 cents. However, to be competitive with the seven-fold lower cost of an acetone-based remover, Applicant believes that the "cost per use" (defined as the bulk price of chemicals required to clean 10 nails) for a GBL-based LNPR must be reduced from 4 cents to approximately ½ cent. This cost reduction would not be possible using the conventional method of applying the LNPR using an absorbent paper or cotton. However, if approximately 50 microliters of LNPR were sufficient for removal of lacquer from each nail, the requisite cost-savings could be obtained. Then, 1 fluid ounce of LNPR would be sufficient for removing lacquer from over 500 nails. By using a small brush or other "zero-waste" application method with a GBL-based LNPR to a nail, it is estimated that 5 to 10-fold less LNPR could be applied (than the amount of acetone which is currently used with a cotton ball applicator) to remove nail polish from a fingernail, and a GBL-based remover could be priced competitively with a conventional acetone or ethyl acetate-based remover.

The efficacy of applying varying amounts of thickened LNPR directly onto the fingernail has been tested. Calibrated volumes of the LNPR were dispensed from a micropipet instrument (Rainin Instrument Company, Woburn, Mass.; Pipetman™ P250) onto a fingernail. In fact, it was determined that a volume of between 10 and 50 microliters of the LNPR containing 99%–99.5% by weight GBL and 0.5%–1.0% KLUCEL™H thickener (see below) was sufficient for coating a fingernail and removing nail polish. As a practical means of applying and spreading these small volumes of thickened LNPR uniformly over a fingernail or toenail, Applicant has employed a conventional nail lacquer applicator brush. Such brushes, which are typically incorporated into the lids which cover nail polish bottles, have bristles which are approximately ¼–½ inch long. As with nail lacquer brushes, the brush (which is attached via a plastic rod to the lower inside surface of the screw-cap lid) is dipped into the GBL-based LNPR and used to "paint" the thickened liquid onto the nail. This simple and cost-effective applicator is re-usable, and as an integral portion of the lid, rests submerged in the LNPR, ready for use, within a 1–2 or 1–3 fluid ounce capacity container. In fact, any small brush, swab or equivalent applicator can be used to dip and transfer a small amount of the thickened LNPR from a container to a nail.

With regard to item (c) above, the thickener described by Helioff et al. would not be suitable for the present invention because of its susceptibility to changes in the pH of the LNPR. That is, repeated entry of the microapplicator [described in (a) above] into the LNPR after contact with the nails and skin is expected to introduce acidic or basic contaminants which will change the pH of the LNPR, causing a loss of viscosity. Thus, the composition of the existing GBL-based LNPR must include a pH-insensitive thickener to avoid viscosity loss in the LNPR due to such pH changes. In addition, the residue resulting from air-drying of the thickened GBL-based LNPR described herein, is conveniently water-soluble, rather than requiring soap or detergent for its removal as described by Helioff et al.

With regard to (d) above, the presently invented GBL-based LNPR product is formulated, packaged and sized to reduce the risk of, and from, accidental ingestion by children. A chemical bittering agent is added to the product to cause oral rejection of the LNPR if it is tasted. The thickened LNPR product is also preferably packaged in a narrow-necked container, reducing or preventing easy child-access to the product inside the container. Finally, the small volume of containers (1–2 ounces) used to hold the LNPR, limits the overall potential harm from accidental product ingestion, relative to the common use of 8 ounce LNPR containers.

Concerning the prior art use of GBL solvent in a LNPR (see U.S. Pat. No. 5,024779), Helioff et al. describe a thickened LNPR whose active solvent is preferably acetone, but may also include methyl ethyl ketone, ethyl acetate, gamma butyrolactone, and mixtures thereof. Helioff et al. require that hydrolyzed, neutralized maleic anhydride-alkyl vinyl ether copolymer cross-linked via a polyethylenenically unsaturated compound is used as the thickener for achieving a smooth cream-like texture. Use of this thickener requires that a pH-neutralizing agent be present in the formulation to maintain a gelled state. A dried coating of the thickener is water-insoluble but can be removed with soap and water. The thickeners used in Day also required use of a neutralizer, indeed a particular neutralizer was required On the other hand, cellulose-derived hydrocolloid thickeners such as hydroxypropylcellulose acetate were previously used for acetone and ethyl acetate LNPRs (e.g., Minton et al., U.S. Pat. No. 4,197,212). It is likely that the granular consistency of cellulosic thickeners dispersed in organic solvents (such as acetone, ethyl acetate and GBL) was found undesirable by Helioff et al. who wished to obtain "a cream-like consistency." This solvent granularity has also been reported elsewhere ("KLUCEL®—Physical and Chemical Properties", brochure #250-2E revised April, 1997 Hercules, Inc. Aqualon Division, Wilmington, Del.).

The thickened LNPR of the present invention is very different from that described by Helioff et al. For example, the selection and physical processing of thickening agent, the compatability of thickener with changes in pH within the LNPR, the use of a narrow-necked container for flow restriction and thereby child safety (to minimize child contact and accidental ingestion of the remover even when it is in use), and the use of a micro-applicator for conserving the product are unique to the present invention. These features are important for making the product safe, effective and cost-efficient. Unlike acetone-based removers, the present remover is non-irritating, non-sensitizing, and substantially non-desiccating to the skin surrounding the nail. Furthermore, the GBL-based nail polish remover is safer to store, handle and ship than an acetone or ethyl acetate-based product because GBL is substantially non-flammable owing to its high flash point (209° F.). While the flammability problem of LNPRs has been addressed previously in U.S. Pat. No. 4,543,206 by Adams, there is a toxicity issue and environmental pollution problem associated with use of his LNPR (based upon methylene chloride).

The following examples illustrate the in vitro effectiveness of propylene glycol-derivative LNPRs as well as GBL-based LNPRs in softening and dissolving commercial nail polishes.

EXAMPLE 1

This example shows that a variety of propylene glycol ethers and propylene glycol ester ethers, with and without modest dilution by water, can rapidly soften and release a single coating of conventional nail polish lacquer (L'Oreal Nail Enamel,#395, L'Oreal Canada, Inc., Montreal, Canada). An in vitro test which was developed to monitor the relative efficacy of different solvents and dilutions thereof is herein described. Approximately one hundred 1 cm$^2$ round spot-coatings of the Revlon nail enamel product were applied by brush to a glass sheet and air-dried for one week before solvent removal experiments were conducted. One commercial acetone-based, and one commercial ethyl acetate-based nail polish remover [CVS brand "Polish Remover-Regular Formula" (containing acetone, water, glycerin and gelatin), and also CVS brand "Nail Polish Remover- Non-Acetone" (containing ethyl acetate, alcohol, castor oil, butyl stearate, and other minor ingredients) both products being distributed by CVS Inc., Woonsocket, R.I.] were respectively used as "control" nail polish remover solvents. These controls helped to determine how rapidly the presently described solvents could loosen a nail polish-lacquer, compared to conventional solvent-based removers. For each trial, a solvent was applied to a nail polish spot coating using a conventional pipe cleaner (a tufted fabric-coated wire which was saturated with the solvent contained in a glass test tube). Each pipe cleaner had been bent into an L-shape prior to solvent-saturation, such that the bottom of the L presented a flat, 1 centimeter long segment to contact the nail polish spot-coating. The solvent-saturated pipe cleaner was gently and continuously rubbed back and forth (approximately one back and forth cycle per second) over the spot coating until the colored nail polish spot had been removed. Using a stop watch, and observing the point in time at which the opaque nail polish visually cleared, it was possible to determine, with good reproducibility, the number seconds of solvent contact with rubbing, required for removal of the nail polish. The time range (in seconds) required to remove each of four essentially identical spot coatings is given.

TABLE I

| SOLVENT (weight %) | LACQUER REMOVAL (seconds) | Solvent CAS No. |
|---|---|---|
| CVS acetone remover (control) | 3.0–3.5 | 67-64-1 |
| CVS ethyl acetate remover (control) | 3.0–3.5 | 141-78-6 |
| 100% PM | 3.5–4.0 | 107-98-2 |
| 90% PM + 10% H$_2$O | 6–7 | |
| 80% PM + 20% H$_2$O | 9–10 | |
| 70% PM + 30% H$_2$O | 30–34 | |
| 100% PMA | 3.0–3.5 | 108-65-6 |
| 90% PMA + 10% H$_2$O | 3.5–4.0 | |
| 100% DPM | 10–12 | 34590-94-8 |
| 100% DPMA | 7–8 | 88917-22-0 |
| 100% PE | 5–5.5 | 52125-53-8 |
| 90% PE + 10% H$_2$O | 7–8 | |
| 80% PE + 20% H$_2$O | 9–10 | |
| 100% PEA | 4–5 | 98516-30-4 |
| 100% PTB | 22–25 | 57018-52-7 |
| 100% DPNB | 25–28 | 29911-28-2 |

Results and Discussion

The PM and PMA solvents were nearly as rapid as acetone and commercial ethyl acetate-based removers in removing a single coating of dried nail polish from a glass plate. The PEA and PE were the next most aggressive, followed by DPMA and DPM. As the overall molecular weight and the size of the ether-linked alkyl side group increased, the time required to loosen and remove the nail polish increased. This may be due to larger solvent molecules having more difficulty penetrating a nail lacquer barrier than smaller molecules, within a given solvent family, i.e., the propylene glycol ether family. As anticipated, dilution of the solvents by water, substantially reduced their rate of loosening and removing a lacquer nail polish. Interestingly, 10% by weight of water reduced the effectiveness of PM somewhat more than it affected PMA. The addition of 5%–10% water to PMA allows convenient thickening of this solvent using a cellulosic thickener such as hydroxypropylcellulose.

EXAMPLE 2

This example shows that gamma butyrolactone (GBL) can rapidly soften and dissolve a double coating of conventional nail polish lacquer (L'Oreal Nail Enamel,#395, L'Oreal Canada, Inc., Montreal, Canada). The same test described in Example 1 was used, except that two coatings of the lacquer were applied to each spot location and dried for one week. GBL, either alone or together with a co-solvent (PM), was thickened with 0.5% by weight hydroxypropylcellulose (KLUCEL®H), and utilized in this experiment. Removers described in Example 1 were also utilized.

TABLE 2

| SOLVENT (weight %) | LACQUER REMOVAL (seconds) | Solvent CAS No. |
|---|---|---|
| CVS acetone remover (control) | 6–7.5 | 67-64-1 |
| CVS ethyl acetate remover (control) | 7–9 | 141-78-6 |
| 99.5% GBL + 0.5% KLUCEL ®H | 8–10 | 96-48-0 |
| 89.5% GBL + 10% PM + 0.5% KLUCEL ®H | 9–11 | |
| 79.5% GBL + 20% PM + 0.5% KLUCEL ®H | 12–14 | |
| 100% PM | 15–18 | 107-98-2 |
| 100% PMA | 14–17 | 108-65-6 |

Results and Discussion

Comparing these results with those in Example 1, the addition of a second coating of nail lacquer nearly doubled the time required for acetone and ethyl acetate to dissolve the coatings. While the GBL solvent was nearly as effective as commercial acetone and ethyl acetate-based removers for removing the double coating of dried nail polish from a glass plate, the PM and PMA removers required additional time.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The gamma butyrolactone and propylene glycol derivative solvent compounds and the other particular described components of the compositions, and the methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, use of other polyethylene glycol derivative solvents or small amounts of co-solvents are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What we claim is:

1. A safety-enhanced packaged liquid nail polish-lacquer removing composition, comprising
   a nail polish-lacquer removing solution which is non-irritating and non-sensitizing to the skin comprising between 51% and 100% by weight of thickened gamma butyrolactone solvent containing at least one PH stable thickening agent that functions in the absence of a neutralizing agent present in an amount effective to produce an absolute kinematic viscosity at 20° C. of from 250–10,000 cp, wherein said solution is packaged in a narrow-necked container, said narrow neck serving to retard or block the flow of said solution when said container is tipped on its side or inverted, and wherein a maximum of 100 ml of said solution is in said container, and
   a reusable applicator device for applying microliter quantities of said solution to each nail.

2. The composition of claim 1, wherein a maximum of 30 ml of said solution is in said container.

3. The composition of claim 1, wherein said applicator device is selected from the group consisting of an applicator brush, porous foam swab or pad, hollow tube, eye dropper, dip stick or combination thereof.

4. The composition of claim 1, wherein said reusable applicator device is attached to a lid which covers said container.

5. The composition of claim 1, further comprising a bittering agent.

6. A liquid nail polish-lacquer removing composition having a thickened, and non-granular consistency, wherein said composition is non-irritating and non-sensitizing to the skin surrounding the fingernails and toenails, and wherein the residue of said composition upon drying, can be rinsed away with water, said composition comprising:

(i) from 51% to 99.9% by weight of gamma butyrolactone organic solvent;
   (ii) from 0.1% to 5% by weight of at least one pH stable thickening agent present in an amount effective to produce an absolute kinematic viscosity at 20° C. of from 250–10,000 cp;
   (iii) optionally, from 0% to 49% of a propylene glycol-derivative co-solvent compound having between 4 and 9 carbon atoms and between 2 and 4 oxygen atoms per molecule, wherein said compound is selected from the group consisting of propylene glycol ethers, dipropylene glycol ethers, propylene glycol ether esters, dipropylene glycol ether esters and combinations thereof;
   (iv) optionally, from 0% to 20% by weight of a humectant/diluent which is selected from the group consisting of water, glycerol, propylene glycol, 1,3-butylene glycol and its isomers, sorbitol and combinations thereof; and
   (v) optionally, from 0% to 10% by weight of an emollient which is selected from the group consisting of fatty acid esters, mineral oil, silicone oil, lanolin, lanolin derivatives and combinations thereof.

7. The nail polish-lacquer removing composition of claim 6 packaged in a narrow-necked container, wherein the narrow neck serves to retard or block the flow of said composition when said container is tipped on its side or inverted, and thereby reduce the possibility of ingestion by children.

8. The nail polish-lacquer removing composition of claim 6, wherein said composition further contains an effective concentration of a bittering agent to reduce the possibility of ingestion by children.

9. The nail polish-lacquer removing composition of claim 6, wherein said composition is packaged in a container containing not more than three fluid ounces of said composition, wherein the limited quantity of said composition in said container serves to limit the potential ingestion hazard to a child.

10. The nail polish-lacquer removing composition of claim 9, wherein said container comprises a reusable applicator device for applying microliter quantities of said composition to each nail.

11. The nail polish-lacquer removing composition of claim 10, wherein said microliter quantities of said composition are between 10 and 100 microliters per nail.

12. The nail polish-lacquer removing composition of claim 10, wherein said container comprises a reusable applicator device selected from the group consisting of an applicator brush, porous foam swab or pad, hollow tube, eye dropper, dip stick or combination thereof.

13. The nail polish-lacquer removing composition of claim 12, wherein said reusable applicator device is attached to a lid which covers said container.

14. The nail polish-lacquer removing composition of claim 6, wherein said composition allows fingernails and toenails to remain free of any sticky residue during the lacquer-removal process, without addition of any electrolyte to said composition.

15. The nail polish-lacquer removing composition of claims 6, wherein the vapors from said solution are non-irritating to the eyes.

16. The nail polish-lacquer removing composition of claim 6, wherein said propylene glycol-derivative co-solvent is selected from the group consisting of propylene glycol methyl ether (PM; 1-methoxy-2-propanol, CAS No. 107-98-2), propylene glycol methyl ether acetate (PMA; 1-methoxy-2-propanol acetate, CAS No. 108-65-6), dipropylene glycol monomethyl ether (DPM; CAS No. 34590-94-8), dipropylene glycol methyl ether acetate (DPMA; CAS No. 88917-22-0), propylene glycol ethyl ether (PE; CAS No. 52125-53-8), propylene glycol ethyl ether acetate (PEA; CAS No. 98516-30-4), propylene glycol n-propyl ether (PNP; CAS No. 1569-01-3), propylene glycol t-butyl ether (PTB; CAS No. 57018-52-7), propylene glycol n-butyl ether (PNB; CAS No. 5131-66-8), and dipropylene glycol n-propyl ether (DPNP, CAS No. 29911-27-1).

17. The nail polish-lacquer removing composition of claim 6, wherein said thickening agent is selected from the group consisting of cease derivatives, natural gums, inorganic thickeners, and synthetic homopolymers and copolymers having from 1 to 30 carbon atoms per monomer unit.

18. The nail polish-lacquer removing composition of claim 17, wherein said thickening agent is a cellulose derivative selected from the group consisting of hydroxycellulose, hydroxyalkylcellulose, and carboxymethylcelluose.

19. The nail polish-lacquer removing composition of claim 18, wherein said hydroxyalkylcellulose thickening agent is selected from the group consisting of hydroxyethylcellulose, hydroxypropylcellulose, and hydroxypropylmethylcellulose.

20. The nail polish-lacquer removing composition of claim 17, wherein said thickening agent is a synthetic homopolymer or copolymer selected from the group consisting of polyacrylic acid esters, polymethacrylic acid esters, polyvinylacetate, and polyvinylpyrrolidone.

21. The nail polish-lacquer removing composition of claim 17, wherein said thickening agent is a natural gum selected from the group consisting of acacia, alginate, carrageenan, guar, karaya, pectin, tragacanth, and xanthan.

22. The nail polish-lacquer removing composition of claim 17, wherein said thickening agent is an inorganic thickener selected from the group consisting of silicas and clays.

23. The nail polish-lacquer removing composition of claim 6, wherein said thickening agent which can function in the absence of a neutralizing agent, can maintain said viscosity with changes in pH, wherein said changes in pH may occur in said composition after a reusable applicator device is repeatedly placed into said composition during nail polish-lacquer removal operations.

24. A nail polish-lacquer removing composition comprising
  from 51% to 99.9% of gamma butyrolactone; and
  at least one pH stable thickening agent which is present in an amount effective to produce an absolute kinematic viscosity at 20° C. of from 250 to 10,000 cp, wherein said thickening agent is not neutralized crosslinked maleic anhydride-alkyl vinyl ether copolymer gel or a neutralized acrylic acid monomer or polymer neutralized with N,N,N',N'-tetrakis (2-hydroxypropyl) ethylaminediamine and 2-ethyl-N-(2-ethylhexyl-1-hexamine.

25. A liquid nail polish-lacquer removing composition which is non-irritating and non-sensitizing to the skin surrounding the fingernails and toenails, wherein said composition comprises between 51% and 100% by weight of gamma butyrolactone solvent, which composition is packaged in a container comprising a reusable applicator device for applying microliter quantities of said composition to each nail.

26. The nail polish-lacquer removing composition of claim 25, wherein said applicator device is selected from the group consisting of an applicator brush, porous foam swab or pad, hollow tube, eye dropper, dip stick or combination thereof.

27. The nail polish-lacquer removing composition of claim 25, wherein said reusable applicator device is attached to a lid which covers said container.

28. The nail polish removing composition of claim 25, wherein said composition further comprises at least one thickening agent capable of functioning in the absence of a neutralizing agent, and which is present in an amount effective to produce an absolute kinematic viscosity at 20° C. or from 250–10,000 cp.

29. The nail polish-lacquer removing composition of claim 28, wherein said composition is packaged in a narrow-necked container, wherein the narrow neck serves to retard or block the flow of said composition when said container is tipped on its side or inverted, and thereby reduce the possibility of ingestion by children.

30. A method of removing a nail polish-lacquer coating from a fingernail or toenail without causing irritation of the skin surrounding the nail, comprising the steps of:
  applying the composition of claim 8 to said coating on said fingernail or toenail;
  allowing the coated fingernail or toenail and said composition to remain in contact for a time sufficient to loosen said coating from said fingernail or toenail, and
  separating and removing said coating and said composition from said fingernail or toenail.

31. A method of conveniently removing a glitter-type nail polish-lacquer coating from a fingernail or toenail without causing irritation of the skin surrounding the nail, comprising the steps of:
  applying the composition of claim 8 to said coating on said fingernail or toenail;
  allowing the coated fingernail or toenail and said composition to remain in contact for a time sufficient to loosen said coating from said fingernail or toenail, and
  separating and removing said coating and said composition from said fingernail or toenail.

* * * * *